United States Patent
Kim et al.

(10) Patent No.: US 8,822,697 B2
(45) Date of Patent: Sep. 2, 2014

(54) PARAMAGNETIC POLYNUCLEAR METAL COMPLEX HAVING HIGH SELF-RELAXATION RATE, PREPARATION METHOD THEREOF, AND CONTRAST MEDIUM CONTAINING SAME

(75) Inventors: Tae Jeong Kim, Gyeongsangbuk-do (KR); Yong Min Chang, Daegu (KR); Hee Kyung Kim, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 273 days.

(21) Appl. No.: 13/393,898

(22) PCT Filed: Nov. 11, 2009

(86) PCT No.: PCT/KR2009/006629
§ 371 (c)(1),
(2), (4) Date: May 25, 2012

(87) PCT Pub. No.: WO2011/027940
PCT Pub. Date: Mar. 10, 2011

(65) Prior Publication Data
US 2012/0226048 A1 Sep. 6, 2012

(30) Foreign Application Priority Data

Sep. 2, 2009 (KR) .................. 10-2009-0082273

(51) Int. Cl.
*C07F 5/00* (2006.01)
*C07D 233/64* (2006.01)
*C07C 229/28* (2006.01)
*C07C 229/24* (2006.01)
*C07C 229/26* (2006.01)
*A61K 49/10* (2006.01)

(52) U.S. Cl.
CPC .............. *C07D 233/64* (2013.01); *C07F 5/003* (2013.01); *C07C 229/26* (2013.01); *C07C 229/28* (2013.01); *C07C 229/24* (2013.01); *A61K 49/103* (2013.01)
USPC ..................... 548/104; 548/312.7; 548/340.1; 556/1; 556/31; 562/565

(58) Field of Classification Search
CPC ..... C07F 5/003; C07D 233/64; C07C 229/24; C07C 229/26; C07C 229/28
USPC .................. 548/104, 312.7, 340.1; 556/31, 1; 562/565
See application file for complete search history.

(56) References Cited

U.S. PATENT DOCUMENTS 5,508,388 A    4/1996    de Learie et al.

FOREIGN PATENT DOCUMENTS

| EP | 1369134 A1 | 12/2003 |
| KR | 10-2007-0117621 A | 2/2007 |
| KR | 10-00879087 B1 | 8/2007 |

OTHER PUBLICATIONS

Aime et al. "Modulation of the Prototropic Exchange Rate at the Water Molecule Coordinated to a GdIII Ion" European Journal of Inorganic Chemistry, 2003, vol. 2003, pp. 2045-2048.*
Sinha et al. "Synthesis and Biological Evaluation of 99mTc-DTPA-bis(His) as a Potential Probe for Tumor Imaging with SPECT" Cancer Biotherapy & Radiopharmaceuticals, 2009, vol. 24, pp. 615-620.*
Caravan, P., Strategies for increasing the sensitivity of gadolinium based MRI contrast agents, Chem. Soc. Rev. 2006, 35, pp. 512-523.
Caravan, P. et al, "Gadolinium (III) Chelates as MRI Contrast Agents: Structure Dynamics and Applications" Chem. Rev. 1999,99, pp. 2293-2352.
Miyake, H. et al., "Novel optically-active bis(amino acid) ligands and their complexation with gadolinium," J. Chem. Soc., Dalton Trans. 2000, pp. 1119-1125.
Werner, E. et al., "High-Relaxivity MRI Contrast Agents: Where Coordination Chemistry Meets Medical Imaging," Angew. Chem. Int. Ed. 2008, 47, pp. 8568-8580.
International Search Report from PCT/KR2009/006629, dated Oct. 7, 2010 (English translation).

* cited by examiner

*Primary Examiner* — Joseph Kosack
(74) *Attorney, Agent, or Firm* — Kenyon & Kenyon, LLP

(57) ABSTRACT

The present invention relates to a paramagnetic polynuclear metal complex having enhanced self-relaxation rate and thermodynamic stability, and more particularly, to a synthetic method of a novel DTPA-bis-amide-histidine ligand and DTPA-bis-amide-aspartic acid ligand, a novel gadolinium complex ([Gd(L)H$_2$O]) using the ligand, and a paramagnetic polynuclear metal complex using the gadolinium complex. The paramagnetic polynuclear metal complex is able to fix three or more metals (one gadolinium and two metal ions), thereby providing more excellent self-relaxation rate than the commercially available contrast agents. Thus, it can be widely applied to an MRI contrast agent because of meeting the high self-relaxation rate required as a contrast agent of magnetic resonance imaging (MRI).

10 Claims, 9 Drawing Sheets

US 8,822,697 B2

PARAMAGNETIC POLYNUCLEAR METAL COMPLEX HAVING HIGH SELF-RELAXATION RATE, PREPARATION METHOD THEREOF, AND CONTRAST MEDIUM CONTAINING SAME

RELATED APPLICATIONS

The present application is a 35 U.S.C. §371 National Phase of International Application No. PCT/KR2009/006629 filed on Nov. 11, 2009, which claims priority to Korean Application No. 10-2009-0082273 filed on Sep. 2, 2009, the disclosure of which is herein incorporated by reference in its entirety.

BACKGROUND OF THE INVENTION

1. Field of the Invention

The present invention relates to a contrast agent used in magnetic resonance imaging. Further, the present invention relates to a ligand having a novel structure, a novel gadolinium complex having high molecular weight and high self-relaxation rate, and a paramagnetic polynuclear metal complex using the same.

2. Description of the Related Art

Magnetic Resonance Imaging (MRI) is a widely used diagnostic imaging technique. Although excellent soft-tissue images can be obtained by MRI; image quality is determined by contrast enhancement of a contrast agent that is used to improve the image. Consequently, the development of the efficient MRI contrast agents has recently drawn ample attention. Thermodynamically stable and paramagnetic Gd(III) ions bearing a multidentate ligand structure and at least one water molecule are expected to exhibit high water relaxivities and therefore suitable candidates for MRI contrast agents. In addition the MRI contrast agents should have chemical inertness, low in vivo toxicity, and should be completely excreted after the diagnostic examination.

Among the early MRI contrast agents approved for use in humans are ionic Gd(III) complexes such as diethylenetriamine-N,N,N',N'',N''-pentaacetate, (N-Me-glucamine)$_2$[Gd(DTPA)(H$_2$O)] (Magnevist, Schering) with a self-relaxation rate of approximately 4.7 mM$^{-1}$s$^{-1}$ (20 MHz, 298 K) and Neutral Gd(III) complexes, such as [Gd(DTPA-bismethylamide)(H$_2$O)] (Omniscan, Nycomed) with a self-relaxation rate of 4.4 mM$^{-1}$s$^{-1}$ (20 MHz, 298 K). However, these contrast agents have the problems of low self-relaxation rate and low thermodynamic stability.

Therefore, studies have been made on the contrast agents having modified DTPA. For example, Korean Patent Publication No. 10-2007-0017621 describes a contrast agent prepared by binding pyridine derivatives at both ends of DTPA, and Korean Patent No. 10-0749087 describes a contrast agent prepared by binding cyclohexane or benzene derivatives at both ends of DTPA. However, since these methods are to improve physical properties attributed to the chemical structure of DTPA, that is, to improve the contrast agent by increasing the water solubility of DTPA, there is a limitation in the improvement of contrast effect.

Further, U.S. Pat. No. 5,508,388 describes a new type of contrast agent prepared by binding amides at both ends of DTPA. However, this patent is suggested to develop a DTPA structure without causing edema, because DTPA causes edema when administered into the human body, and thus it is not concerned with the improvement of contrast effect.

The present inventors have studied to develop various chemical structures for the improvement of contrast effect. As a result, they found that three or more metals are fixed by binding of various metal ions so as to increase the stability in the binding between metal ions and ligands and the self-relaxation rate, thereby completing the present invention.

SUMMARY OF THE INVENTION

In order to solve the above problems, an object of the present invention is to provide a ligand capable of fixing three or more metals (one gadolinium and two metal ions) by binding of various metal ions (sodium, potassium, copper, zinc, magnesium, calcium), a preparation method thereof, and a contrast agent comprising the same, thereby providing a gadolinium complex having high self-relaxation rate and thermodynamic stability.

Effect of the Invention

Unlike the conventional contrast agents, the novel DTPA-bis-amide-histidine ligand and DTPA-bis-amide-aspartic acid ligand, the gadolinium (Gd) complex thereof, and the paramagnetic polynuclear metal complex thereof according to the present invention have three or more metals (one gadolinium and two metal ions). Therefore, compared to the contrast agents having only gadolinium metal ion, they i) have more excellent contrast effect and thermodynamic stability, ii) improve image quality by higher contrast effect when practically used as a contrast agent, iii) include DTPA as a basic structure to have chemical inertness and low in vivo toxicity, and are completely excreted after the diagnostic examination. Accordingly, they can be widely applied to an MRI contrast agent because of meeting the high self-relaxation rate required as a contrast agent of magnetic resonance imaging (MRI).

DETAILED DESCRIPTION OF THE PREFERRED EMBODIMENTS

Figure 1:
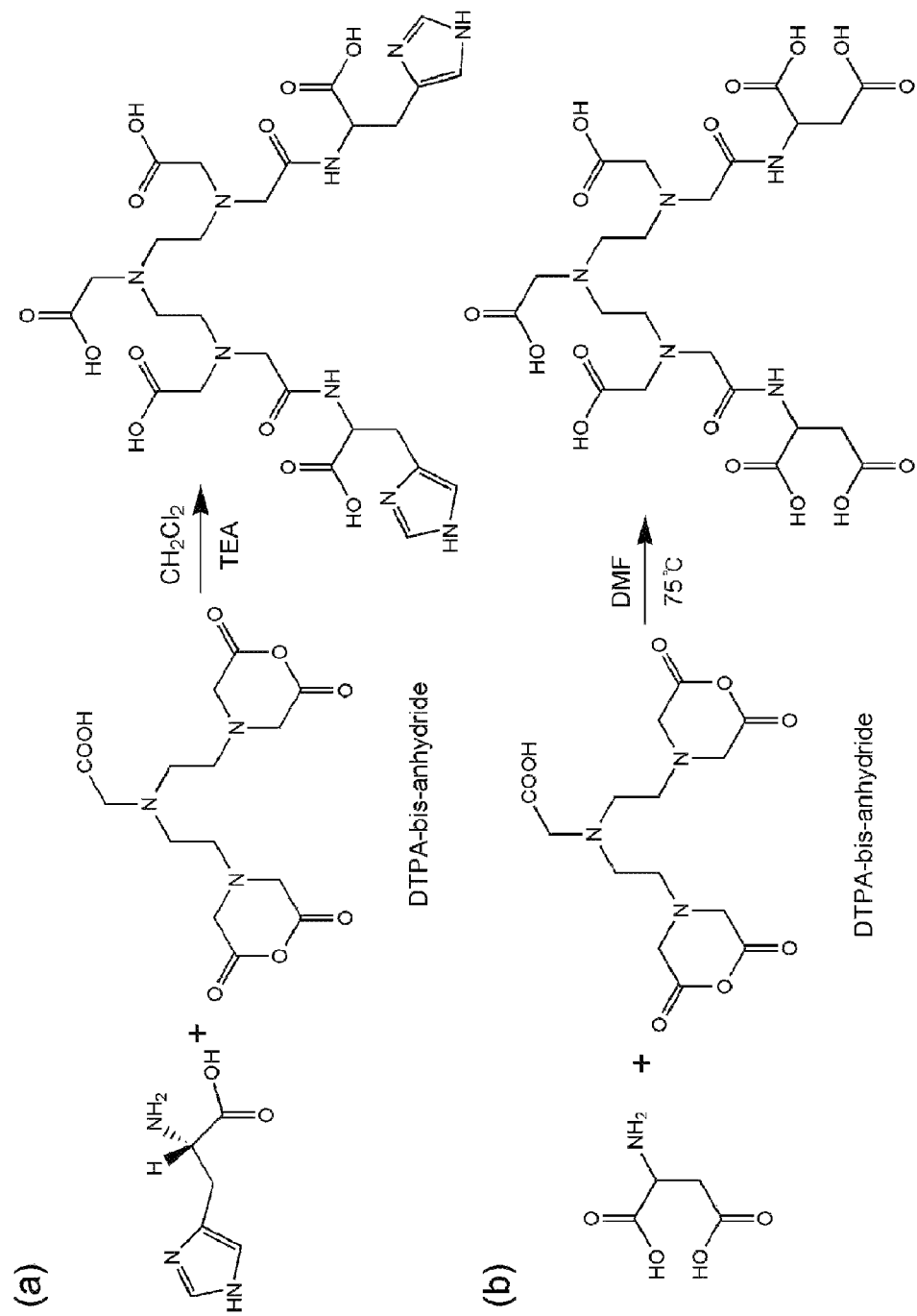
FIG. 1 shows the synthetic method of a DTPA-bis-amide-histidine ligand (L1) and a DTPA-bis-amide-aspartic acid ligand (L2)

The present invention provides a novel DTPA-bis-amide-histidine ligand and a novel DTPA-bis-amide-aspartic acid ligand, a gadolinium (Gd) complex thereof, and a paramagnetic polynuclear metal complex thereof. Further, the present invention provides a synthetic method thereof. The paramagnetic polynuclear metal complex of the present invention has three or more metals (one gadolinium and two metal ions) to show high self-relaxation rate, thereby providing a desirable contrast agent.

Accordingly, the present invention provides a compound having the following Formula 1, which can be prepared from DTPA and histidine or aspartic acid.

[Formula 1]

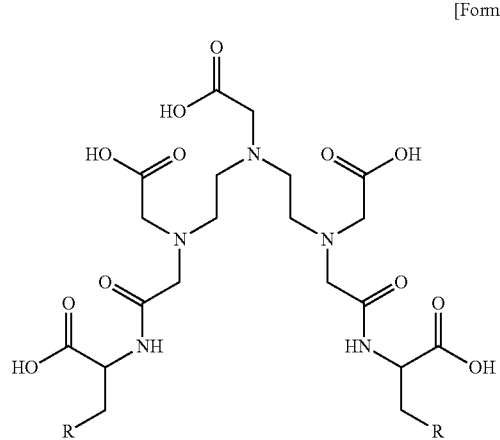

wherein R is

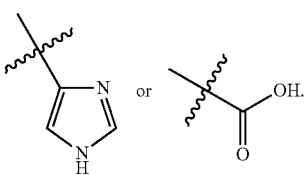

As used herein, the term "DTPA" is an abbreviation for a metal affinity chelate compound, DiethyleneTriamine PentaAcetic acid, and it is a radiation-protective agent. The protective agent acts to remove radioactive substances from the body, thereby reducing cytotoxicity.

The compound of Formula 1 is characterized in that the DTPA structure binds with histidine or aspartic acid. Owing to each structural property, the compound may have three or more metals (one gadolinium and two metal ions) unlike the compounds used as the conventional contrast agents. In addition, it has three or more metals (one gadolinium and two metal ions), thereby showing high contrast-enhancing effect and high thermodynamic stability.

Further, the present invention provides a gadolinium complex of a compound represented by the following Formula 2.

[Formula 2]

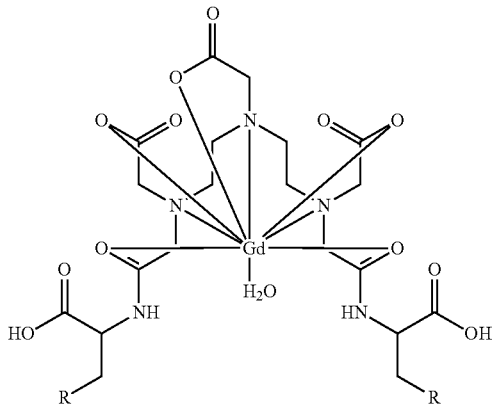

wherein R is

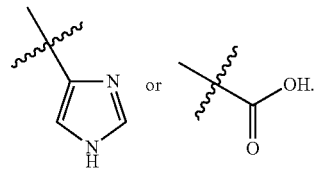

As used herein, the term "complex" refers to a cluster formed by steric coordination of one or more central atoms or ions with other atoms, ions, molecules, or atomic groups in a particular orientation. Herein, atoms, ions, molecules, or atomic groups coordinated to the central atoms or ions are called ligand. A complex is generally marked using square bracket ([ ]) in Formula. The bond between the central atom and the ligand is an ionic bond or covalent bond, and the number of ligand includes atomic groups even though they are not charged.

The compound of Formula 2 means complex formation between the compound of Formula 1 and gadolinium. In this regard, gadolinium forms the complex by the structural characteristic of DTPA, and the structure of histidine or aspartic acid does not contribute to the complex formation. Therefore, the structure of histidine or aspartic acid is characterized in that it can form a complex with other metals.

Further, the present invention provides a paramagnetic polynuclear metal complex represented by the following Formula 3.

[Formula 3]

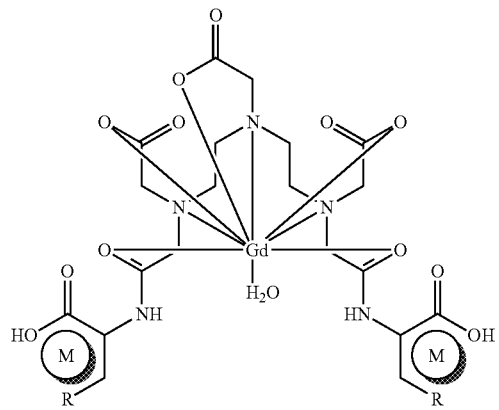

wherein R is

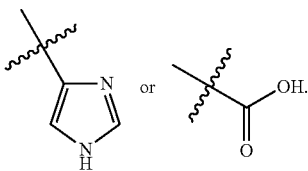

The paramagnetic metal used in the present invention is not particularly limited, as long as it can be used as a contrast agent. Considering that it is used together with gadolinium and the contrast effect, sodium, potassium, magnesium, calcium, copper, or zinc is preferable, and copper is most preferable.

Further, the present invention provides a method for preparing the compound represented by Formula 1, comprising the following steps of:

1) adding histidine or aspartic acid to DTPA-bis-anhydride, followed by stirring (step 1);
2) removing a solvent from the mixture prepared in step 1 under low pressure, and then dissolving the resultant in methanol, followed by silica gel chromatography (step 2);
3) precipitating the resulting mixture obtained in step 2 in acetone (step 3); and
4) drying the substance obtained in step 3 under vacuum to obtain a compound (step 4).

In step 1, if histidine is used, $CH_2Cl_2$ (15 mL) is preferable as a solvent, and if aspartic acid is used, DMF (N,N-dimethylformamide) is preferable as a solvent.

Step 2 is a step of purifying the compound that is prepared by termination of the reaction of step 1, in which the solvent is completely removed under low pressure, and then dissolved in methanol, followed by silica gel chromatography.

Step 3 is a step of obtaining a gadolinium complex, in which cold acetone is used to precipitate the gadolinium complex, and the gadolinium complex can be obtained.

Step 4 is a step of finally obtaining the compound purified by silica gel chromatography, in which the resultant of step 3 is dried under vacuum to obtain the compound. At this time, the drying process is preferably performed above room temperature.

Further, the present invention provides a method for preparing a gadolinium complex of the compound represented by Formula 2, comprising the following steps of:

1) adding the compound represented by Formula 1 to distilled water, and then adding $Gd_2O_3$ thereto to prepare a solution mixture by stirring (step 1);
2) removing impurities and the solvent from the solution mixture prepared in step 1 (step 2);
3) dissolving the resultant prepared in step 2 in deionized water, and then precipitating it in acetone to obtain a solid.

Step 1 is a step of forming a gadolinium complex, in which a molar ratio of the compound represented by Formula 1 and $Gd_2O_3$ is preferably 1 or more considering the yield of the gadolinium complex.

Step 2 is a step of removing impurities and the solvent, in which impurities may be removed using Celite.

Step 3 is a step of finally obtaining the gadolinium complex, in which cold acetone is used to precipitate the gadolinium complex, and the gadolinium complex can be finally obtained.

Further, the present invention provides a method for preparing the paramagnetic polynuclear metal complex represented by Formula 3, comprising the following steps of:

1) adding paramagnetic metal ions to the gadolinium complex of the compound represented by Formula 2 to prepare a solution mixture (step 1); and
2) adding solution mixture prepared in step 1 to acetone for precipitation, and then drying it by filtration to remove the paramagnetic metal ions that are not reacted with the gadolinium complex (step 2).

Step 1 is a step of forming the paramagnetic polynuclear metal complex, in which a molar ratio of the paramagnetic metal ion and the compound represented by Formula 2 is preferably 2 or more considering the yield of the paramagnetic polynuclear metal complex. The paramagnetic metal ion is preferably sodium, potassium, magnesium, calcium, copper, or zinc ion.

Step 2 is a step of finally obtaining the paramagnetic polynuclear metal complex, in which cold acetone is used to precipitate the paramagnetic polynuclear metal complex, and the paramagnetic polynuclear metal complex can be finally obtained.

Further, the present invention provides a contrast agent including the paramagnetic polynuclear metal complex represented by Formula 3.

Unlike the conventional contrast agents, the contrast agent according to the present invention has three or more metals (one gadolinium and two metal ions), thereby showing high contrast-enhancing effect and high thermodynamic stability.

Hereinafter, the preferred Examples with drawings and tables are provided for better understanding. However, these Examples are for illustrative purposes only, and the invention is not intended to be limited by these Examples.

All reactions according to the following Examples were carried out under nitrogen atmosphere using the standard Schlenk techniques. Solvents required in the experiments were also dried in advance. All commercial reagents were purchased from Aldrich. Deionized water was used for all experiments.

Example 1-1

Preparation of DTPA-bis-amide-histidine (L1) of Formula 1

To a stirred suspension of 0.765 g (4 mmol) of histidine in $CH_2Cl_2$ (15 mL) was added 5 mL of triethylamine. The mixture was stirred at room temperature (25° C.) for hour. After 1 hour-stirring, 0.71 g (2 mmol) of DTPA-bis-anhydride was added, and further stirred for 6 hours, and then the solvent was removed under low pressure, and the residue was dissolved in 5 mL of methanol. The solution was passed through a short column of silica gel (60 mesh) with methanol. The eluate was precipitated in 250 mL of acetone, followed by filtration. The obtained white solid product was dried under vacuum at 50° C. for 8 hours. FIG. 1(a) is a schematic diagram of the synthetic method.

Example 1-2

Preparation of DTPA-bis-amide-aspartic acid (L2) of Formula 1

Figure 4:
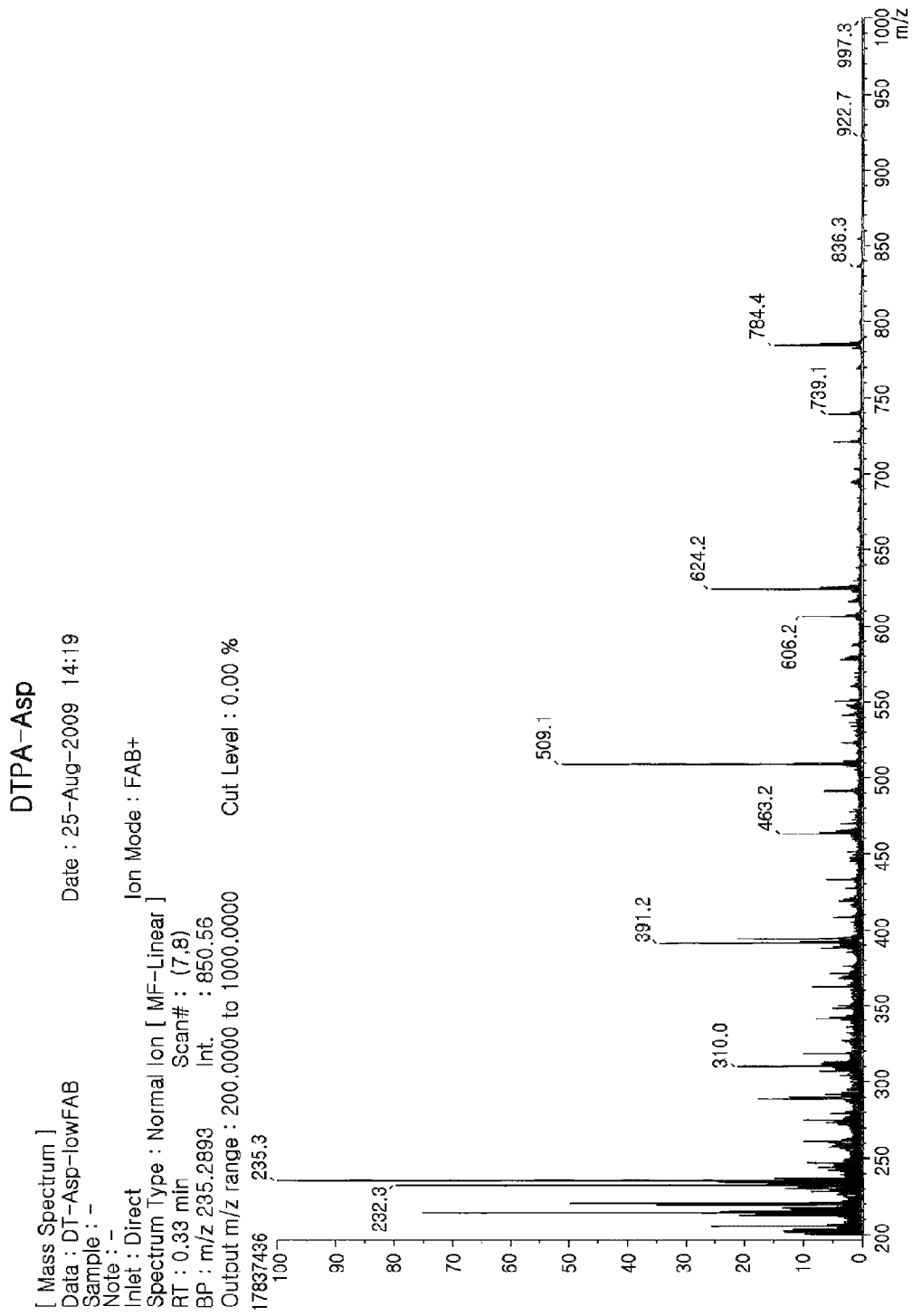
FIG. 4 shows the results of Maldi-TOF mass spectrometry for aspartic acid (L2)

To a stirred suspension of 0.71 g (2 mmol) of DTPA-bis-anhydride in 15 mL of N,N-dimethylformamide (DMF) was added 0.53 g (4 mmol) of aspartic acid. The mixture was stirred at 75° C. for 12 hours, and the solvent was completely removed under low pressure, and the residue was dissolved in 10 mL of methanol. The solution was passed through a short column of silica gel (60 mesh) with methanol. The eluate was precipitated in 250 mL of acetone, followed by filtration. The obtained white solid product was dried under vacuum at 65° C. for 10 hours. FIG. 1(b) is a schematic diagram of the synthetic method, and the result of Maldi-TOF mass spectrometry is shown in FIG. 4.

Example 2-1

Preparation of Gadolinium Complex ([Gd(L1)H$_2$O].2.5H$_2$O))

Figure 2:
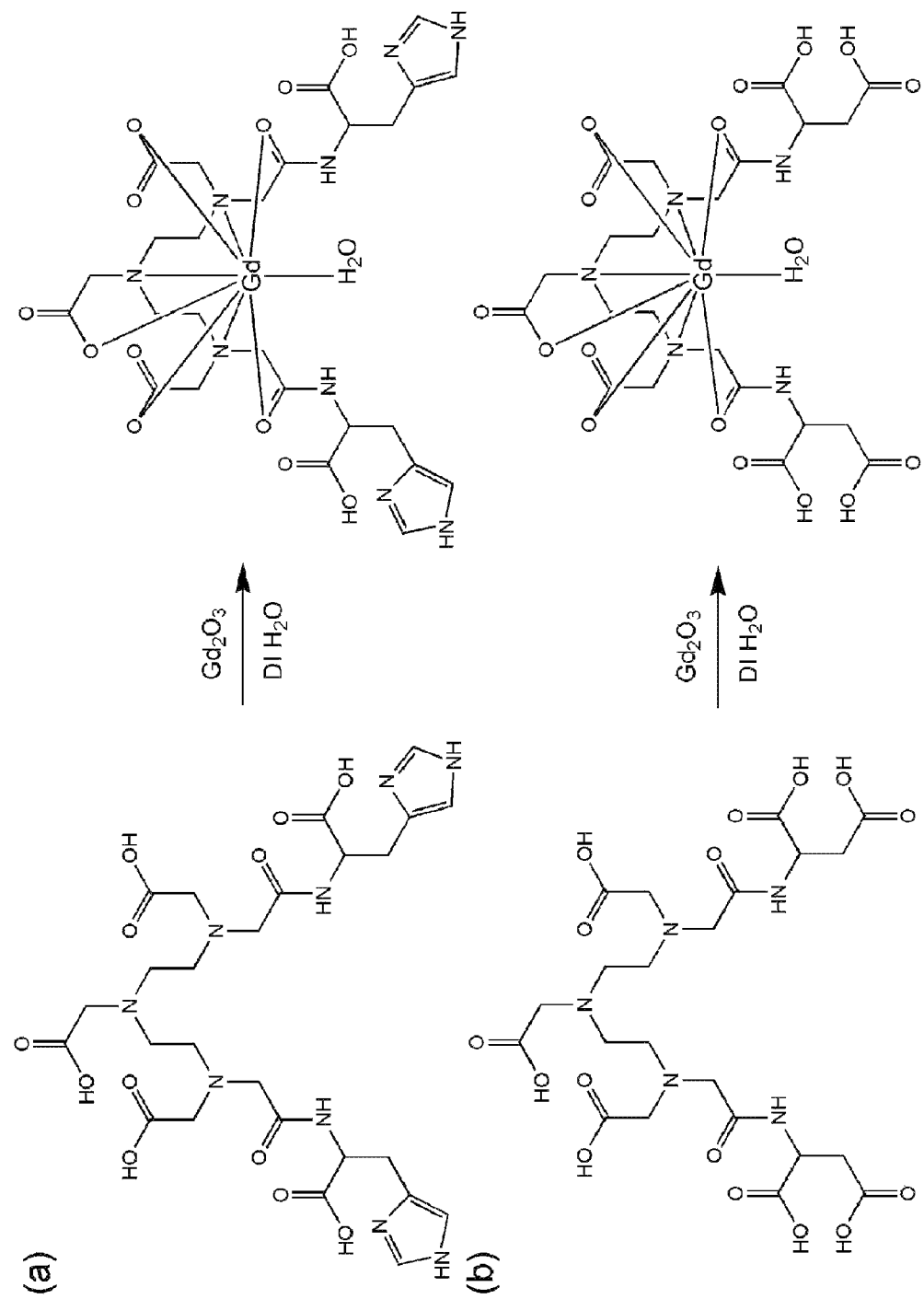
FIG. 2 shows the synthetic method of novel gadolinium complexes ([Gd(L1)H$_2$O] and [Gd(L2)H$_2$O]) using the ligands (L1 and L2)

To a solution of 0.67 g (1 mmol) of DTPA-bis-amide-histidine (L1) prepared in Example 1-1 in 10 mL of deionized water was added 0.18 g (0.5 mmol) of Gd$_2$O$_3$. The suspension was stirred at 90° C. for 6 hours. A clear yellow solution was passed through Celite to completely remove insoluble impurities and then to remove the solvent. The residue was fully dissolved in 5 mL of deionized water, and precipitated in 250 mL of cold acetone. The white solid precipitate was filtered and dried. FIG. 2(a) is a schematic diagram of the synthetic method.

Figure 5:
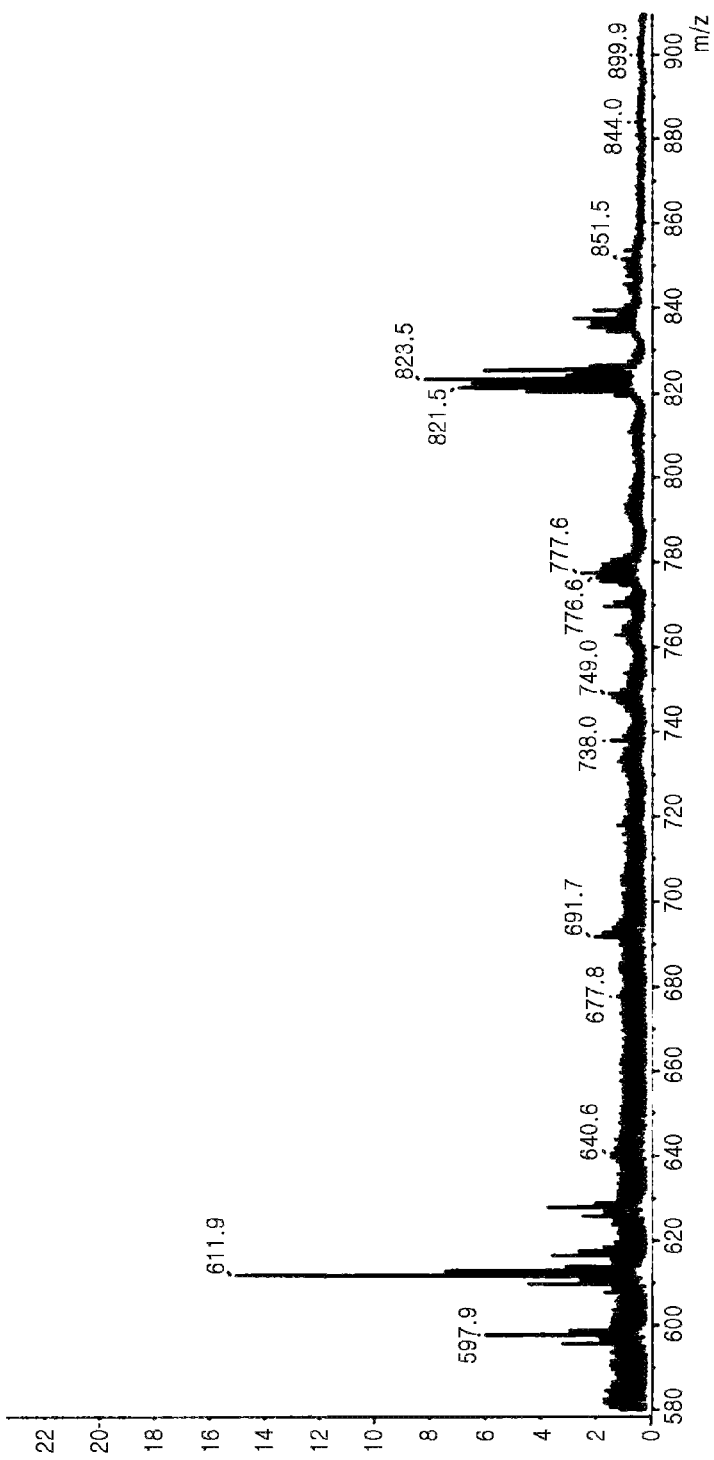
FIG. 5 shows FABMS data obtained after synthesis of the gadolinium complex of DTPA-bis-amide-histidine ligand (L1)

The prepared compound was analyzed by elemental analysis and mass spectrometry as follows. FIG. 5 shows the specific data of FABMS.

Calc.: C, 35.29; H, 4.67, N, 14.25.
Found: C, 35.39; H, 4.42, N, 13.84.
FABMS (m/z): 821.50 (M-H$_2$O)$^+$ Example 2-2

Preparation of Gadolinium Complex ([Gd(L2) H$_2$O].3E$_2$O))

A gadolinium complex of DTPA-bis-amide-aspartic acid (L2) was synthesized in the same manner as in the synthetic method of the gadolinium complex of DTPA-bis-amide-histidine (L1), which is described in Example 2-1. FIG. 2(b) is a schematic diagram of the synthetic method.

Figure 6:
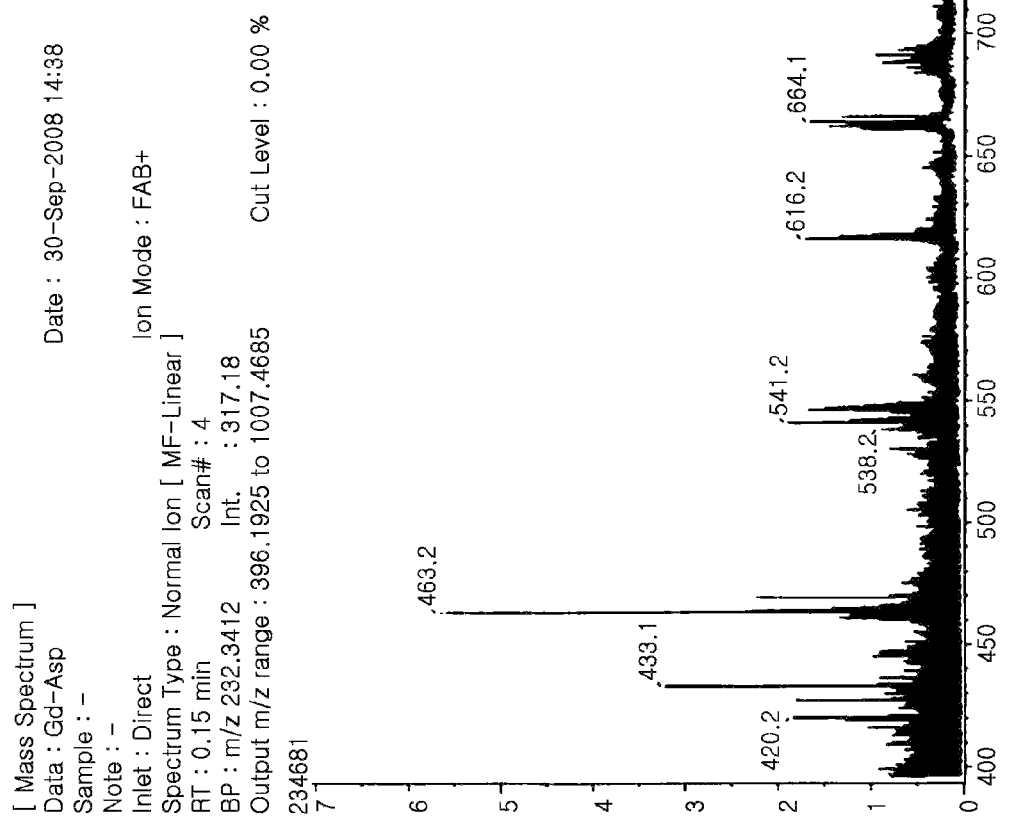
FIG. 6 shows FABMS data obtained after synthesis of the gadolinium complex of DTPA-bis-amide-aspartic acid ligand (L2)
Figure 7:
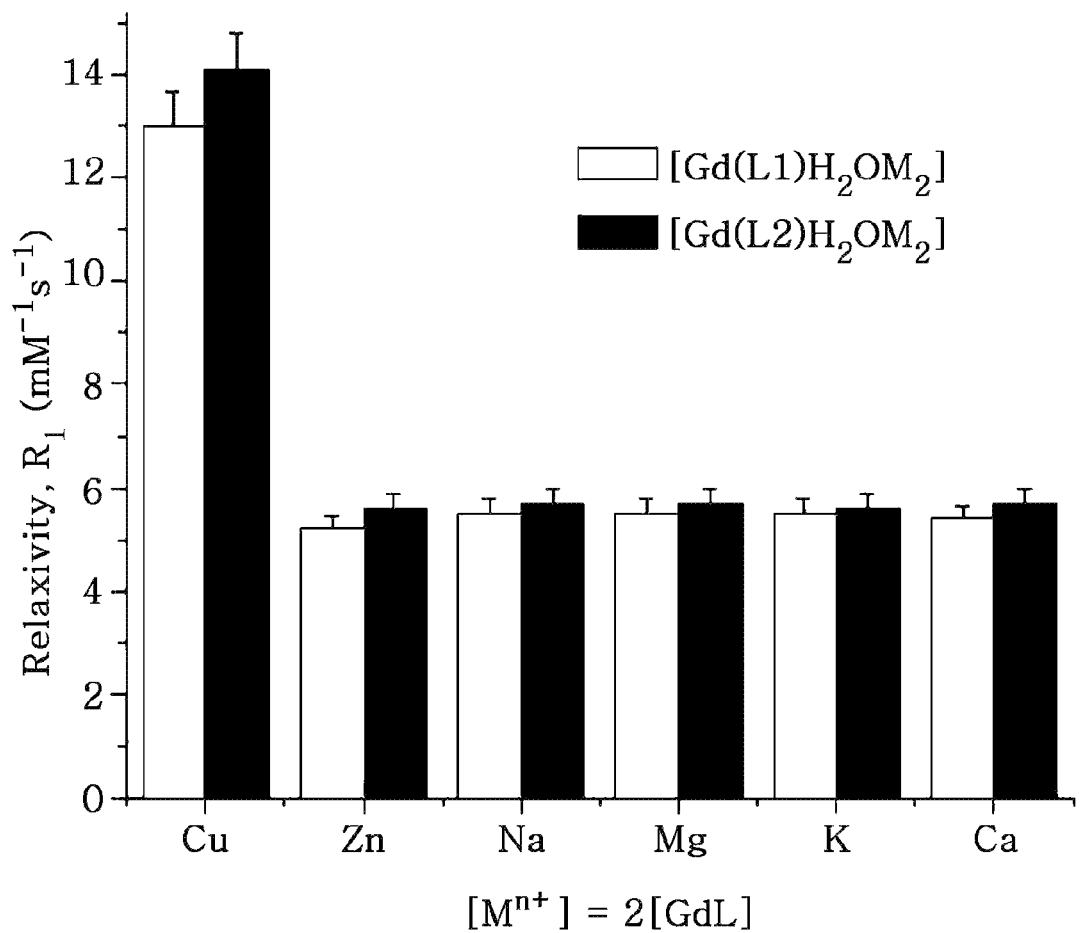
FIG. 7 is a graph showing self-relaxation rates (R1) of the gadolinium complex ([Gd(L)H$_2$O]) and the paramagnetic polynuclear metal complex [Gd(L)H$_2$OM$_2$], K$^+$, Mg$^{2+}$, Ca$^{2+}$, Cu$^{2+}$ or Zn$^{2+}$, based on the values of FIG. 4.
Figure 8:
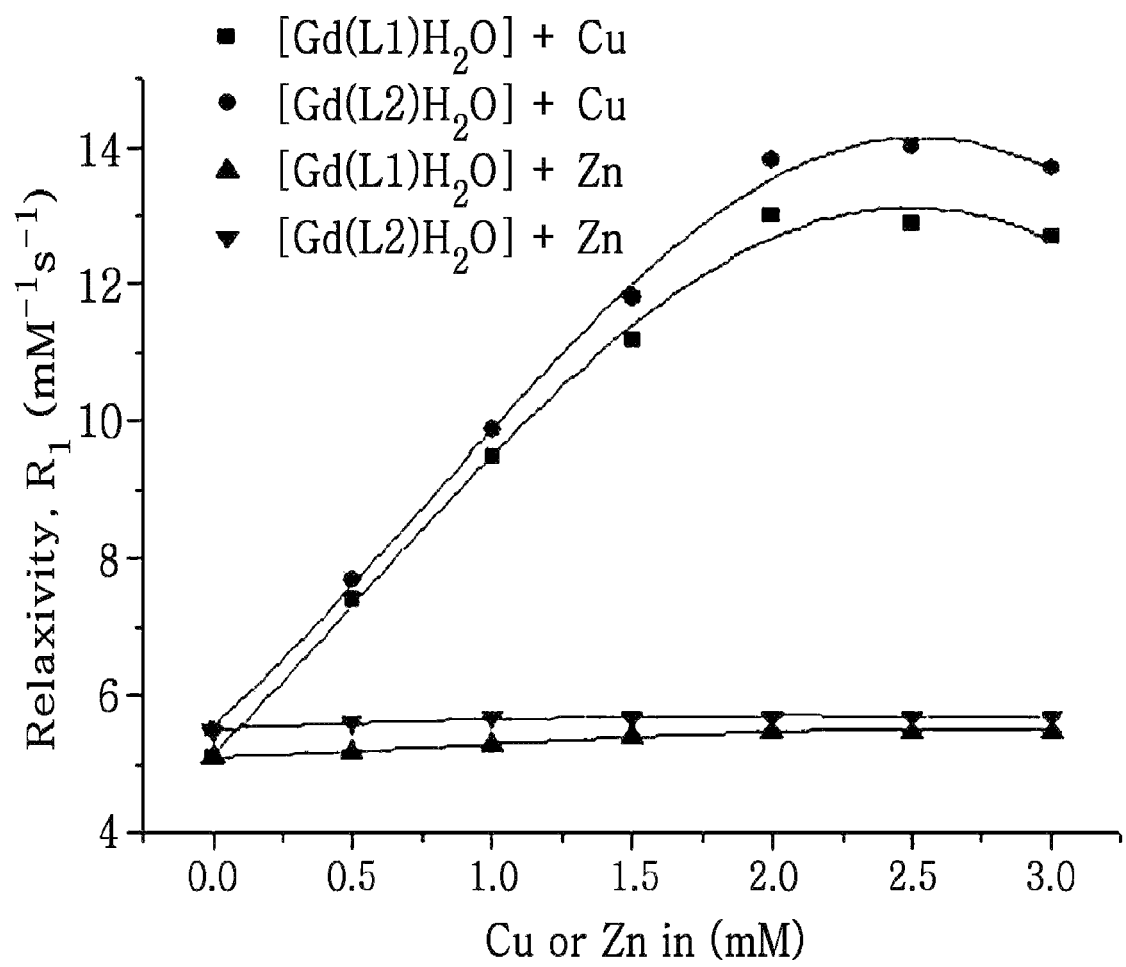
FIG. 8 is a graph showing self-relaxation rates (R1) of the paramagnetic polynuclear metal complex [Gd(L)H$_2$OM$_2$] according to an increase in the concentration of M=Cu, Zn.

The prepared compound was analyzed by elemental analysis and mass spectrometry as follows. FIG. 6 shows the specific data of FABMS.

Calc.: C, 31.09; H, 4.46, N, 8.24.
Found: C, 31.50; H, 4.51, N, 8.24.
FABMS (m/z): 778.15 (M-H$_2$O)$^+$ Example 3

Preparation of Paramagnetic Polynuclear Metal Complex [Gd(L)H$_2$OM$_2$], M=N$^+$, K$^+$, Mg$^{2+}$, Ca$^{2+}$, Cu$^{2+}$ and Zn$^{2+}$))

Figure 3:
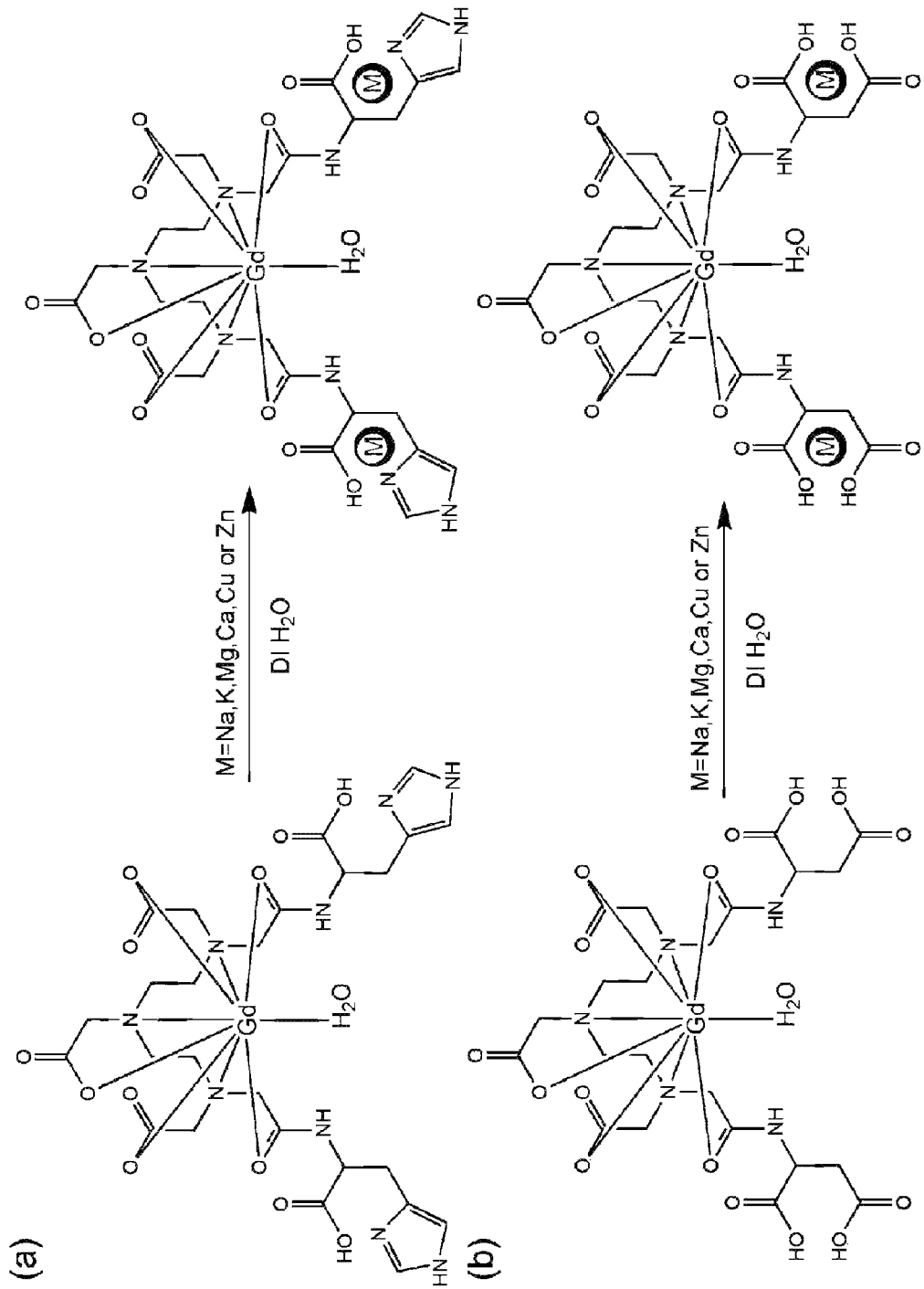
FIG. 3 shows the synthetic method of paramagnetic polynuclear metal complexes ([Gd(L)H$_2$OM$_2$], M=Na$^+$, K$^+$, Mg$^{2+}$, Ca$^{2+}$, Cu$^{2+}$ or Zn$^{2+}$) using the gadolinium complexes ([Gd(L1)H$_2$O] and [Gd(L2)H$_2$O])

2 mol of ion to be synthesized are added to 1 mol of the gadolinium complex ([Gd(L1)H$_2$O] or [Gd(L2)H$_2$O]) prepared in Example 2-1 or 2-2, and then mixed with each other. At this time, NaCl (Sodium chloride), KCl (Potassium chloride), MgSO$_4$ (Magnesium sulphate), CaCl$_2$ (Calcium chloride), Cu(NO$_3$)$_2$ (Copper Nitrate), and Zn(NO$_3$)$_2$ (Zinc Nitrate) were used as a substance providing metal ions. To remove metal ions that were not reacted with the gadolinium complex, the mixture was precipitated in cold acetone, and dried by filtration. FIG. 3 is a schematic diagram of the synthetic method.

In the following Experimental Examples, equilibrium constants, stability constants, selectivity constants, and conditional stability constants of the compounds of Formula 1 (L1 and L2) and the gadolinium complexes ([Gd(L1)H$_2$O] and [Gd(L2)H$_2$O]) of Examples were measured. In addition, self-relaxation rates of the gadolinium complexes ([Gd(L1)H$_2$O] and [Gd(L2)H$_2$O]), and the paramagnetic polynuclear metal complexes ([Gd(L1)H$_2$OM$_2$] and [Gd(L2)H$_2$OM$_2$], M=Na$^+$, K$^+$, Mg$^{2+}$, Ca$^{2+}$, Cu$^{2+}$ or Zn$^{2+}$) were measured, and compared with that of Omniscan which is widely known as a paramagnetic contrast agent.

Experimental Example 1

Measurement of Protonation Equilibrium Constant, Stability Constant, Selectivity Constant, Conditional Stability Constant, and pM Value Protonation equilibrium constants ($K_iH$) of the ligand L1 and L2 prepared in Examples 1-1 and 1-2, and stability constants ($K_{ML}$), selectivity constants ($K_{Sel}$) and conditional stability constants ($K'_{Sel}$) of the gadolinium complex ([Gd(L)]), and pM values (affinity between ligand and metal) of gadolinium (Gd(III)), calcium (Ca(II)), zinc (Zn(II)), and copper (Cu(II)) at pH 7.4 were shown in the following Table 1.

The protonation equilibrium constant ($K_iH$) can be defined by the equation of $K_iH=[H_iL]/[H_{i-1}L][H^+]$, wherein HiL is a protonated ligand (i=1, 2, . . . ).

The stability constant ($K_{ML}$) can be defined by the equation of $K_{ML}=[ML]/[M][L]$, wherein M is Gd, Ca, Zn, Cu, and L indicates a ligand.

The pM value can be defined by the equation of pM=-log [M$^{n+}$] at pH=7.4.

[M]=1.0 µmol/dm$^3$, [L]=1.1 µmol/dm$^3$

TABLE 1

| Equilibrium | L1 | L2 | Omniscan |
|---|---|---|---|
| [HL]/[L][H] | 9.52 | 11.55 | 9.37 |
| [H$_2$L]/[HL][H] | 7.59 | 9.42 | 4.38 |
| [H$_3$L]/[H$_2$L][H] | 6.52 | 5.92 | 3.31 |
| [H$_5$L]/[H$_4$L][H] | 3.82 | 2.04 | — |
| ΣpKa | 27.45 | 28.93 | 17.06 |
| [GdL]/[Gd][L] | 19.59 | 21.12 | 16.85 |
| {log K$_{GdL}$(PH 7.4)} | 17.03 | 14.93 | 14.84 |
| [CaL]/[Ca][L] | 6.86 | 10.18 | 7.17 |
| {log K$_{CaL}$(PH 7.4)} | 4.30 | 4.01 | 5.11 |
| [ZnL]/[Zn][L] | 10.93 | 14.67 | 12.04 |
| {log K$_{ZnL}$(pH 7.4)} | 8.37 | 8.48 | 10.02 |
| [CuL]/[Cu][L] | 10.98 | 14.78 | 13.03 |
| {log K$_{CuL}$(pH 7.4)} | 8.42 | 8.59 | 11.06 |
| [log K$_{sel}$(Gd/Ca)] | 12.73 | 10.92 | 9.68 |
| [log K$_{sel}$(Gd/Zn)] | 8.66 | 6.45 | 4.81 |
| [log K$_{sel}$(Gd/Cu)] | 8.66 | 6.34 | 3.82 |
| log K'$_{sel}$ | 19.59 | 10.74 | 9.03 |
| pGd | 16.03 | 13.98 | 13.88 |
| pCa | 3.30 | 30.1 | 4.19 |
| pZn | 7.37 | 7.48 | 9.06 |
| pCu | 7.42 | 7.59 | 10.05 | log K (25° C., µ = 0.10M (KCl))
pM = -log[Mn+] free at pH 7.4; [Mn+] total = 1 µmol/dm3 [L]tatal = 1.1 µmol/dm3

When the gadolinium complex ([Gd(L)H$_2$O]) is used as a contrast agent, gadolinium may generate cytotoxicity by separation of gadolinium from the ligand in the human body. Thus, more stable and stronger affinity of gadolinium for the ligand is preferable for prevention of the separation.

As shown in Table 1, the ligand (L) and the gadolinium complex ([Gd(L)]) had higher protonation equilibrium constant ($K_iH$), stability constant ($K_{ML}$), selectivity constant ($K_{sel}$), conditional stability constant ($K'_{Sel}$), and pM value than Omniscan, indicating the binding between the metal and ligand is stable enough to be used as a desirable contrast agent.

Experimental Example 2

Measurement of Self-Relaxation Rate (Relaxivity)

The self-relaxation rates R1 of the gadolinium complexes ([Gd(L)H$_2$O]) prepared in Examples 2-1 and 2-2 and the paramagnetic polynuclear metal complexes ([Gd(L)H$_2$OM$_2$], M=Na$^+$, K$^+$, Ca$^{2+}$, Cu$^{2+}$ or Zn$^{2+}$) prepared in Example 3 were measured. A contrast agent having higher self-relaxation rate shows high contrast effect even though a smaller amount thereof is administered. Thus, the self-relaxation rate is a factor that determines the efficiency of contrast agent in magnetic resonance imaging.

T1 (relaxation time) measurements were carried out using an inverse recovery method with a variable conductance time (TI) at 1.5 T (64 MHz). The magnetic resonance (MR) images were acquired at 35 different T1 values ranging from 50 to 1750 msec. T1 was obtained from the non-linear least square fit of the signal intensity measured at each TI value. Relaxivity (R1) was then calculated as an inverse of relaxation time per mM. The results are shown in the following Table 2.

TABLE 2

| Complex | R1 (mM$^{-1}$s$^{-1}$) | |
|---|---|---|
| | L1 | L2 |
| [Gd(L)H$_2$O] | 5.9 ± 0.03 | 6.9 ± 0.04 |
| [Gd(L)H$_2$O•Cu$_2$] | 13.0 ± 0.25 | 14.1 ± 0.21 |
| [Gd(L)H$_2$O•Zn$_2$] | 5.2 ± 0.26 | 5.6 ± 0.28 |
| [Gd(L)H$_2$O•Na$_2$] | 5.5 ± 0.27 | 5.7 ± 0.28 |
| [Gd(L)H$_2$O•Mg$_2$] | 5.5 ± 0.27 | 5.7 ± 0.28 |
| [Gd(L)H$_2$O•K$_2$] | 5.5 ± 0.27 | 5.6 ± 0.28 |
| [Gd(L)H$_2$O•Ca$_2$] | 5.5 ± 0.27 | 5.7 ± 0.28 |
| Omniscan | 3.3 ± 0.03 | |

As shown in Table 2, the gadolinium complexes ([Gd(L)H$_2$O]) and the paramagnetic polynuclear metal complexes [Gd(L)H$_2$OM$_2$], (M=Na$^+$, K$^+$, Mg$^{2+}$, Ca$^{2+}$, Cu$^{2+}$ or Zn$^{2+}$) excluding Cu showed approximately twice higher self-relaxation rate than Omniscan, and the gadolinium-Cu complex showed three to four times higher self-relaxation rate than Omniscan. Thus, the present invention provides a contrast agent capable of effectively enhancing signal intensity.

Experimental Example 3

MRI Test

In order to examine the contrast effect of the paramagnetic polynuclear metal complex ([Gd(L)H$_2$OCu$_2$]) prepared in Example 3 on the hepatocellular carcinoma cells, T1-weighted images were obtained from H-ras 12V transgenic mouse bearing hepatocellular carcinoma.

Figure 9:
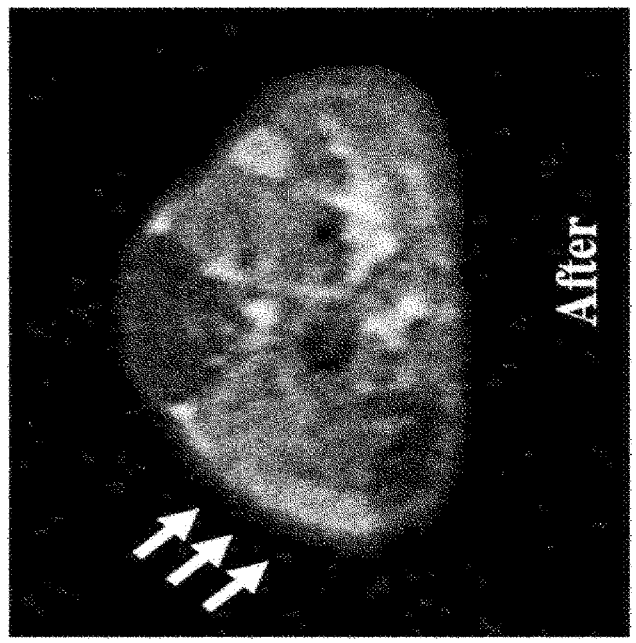
FIG. 9 shows the T1-weighted MRI images of the hepatocellular carcinoma bearing H-ras 12 v transgenic mouse before and after injection of the contrast agent, in order to examine the contrast effect of the paramagnetic polynuclear metal complex [Gd(L)H$_2$OCu$_2$] on hepatocellular carcinoma cells (tumor is indicated by arrows).
Figure 9:
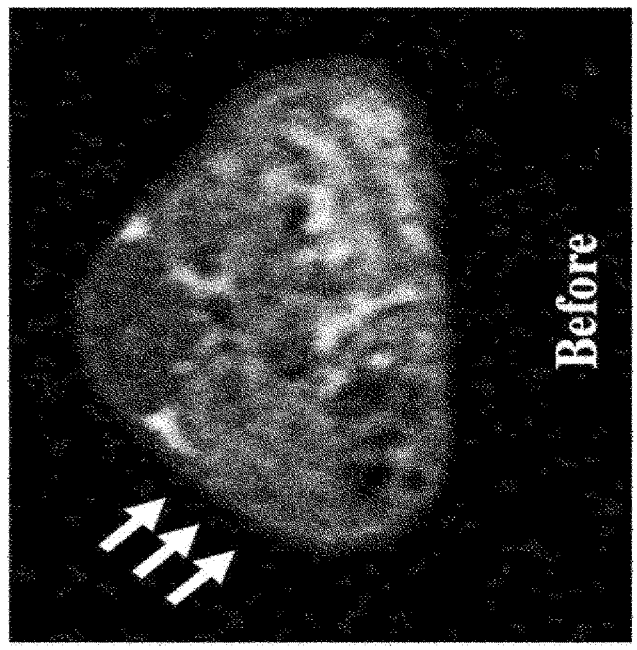

MR images were obtained using a 1.5T magnetic resonance scanner (GE Signa Advantage, GE Medical system, USA) by T1-weighted spin-echo imaging. 1.43 mmol/Kg of [Gd(L)H$_2$OCu$_2$] was injected into a tail vein of the anaesthetized mouse, and the images were obtained before and after injection. The results are shown in FIG. 9. As shown in FIG. 9, enhanced signal intensity (brighter) was observed in hepatocellular carcinoma (indicated by arrows) after injection of [Gd(L)H$_2$OCu$_2$].

INDUSTRIAL APPLICABILITY

Unlike the conventional contrast agents, the ligand and the paramagnetic polynuclear metal complex including the ligand according to the present invention have three or more metals (one gadolinium and two metal ions) to show more excellent contrast effect and thermodynamic stability than the contrast agent having only gadolinium metal ion. Thus, when it is used as a contrast agent in the body, stability and image quality are improved by higher contrast effect than the conventional contrast agents. In addition, owing to the DTPA structure, it has chemical inertness and low in vivo toxicity, and should be completely excreted after the diagnostic examination. Therefore, it can be effectively used as an MRI contrast agent for diagnostic imaging.

What is claimed is:

1. A compound represented by the following Formula 1:

[Formula 1]

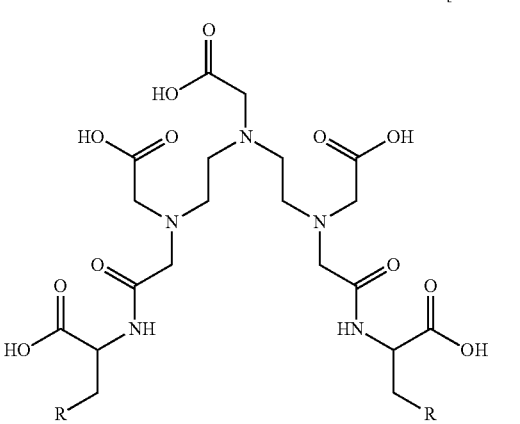

wherein R is

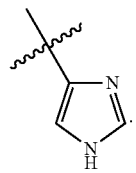 [SMILES: *c1c[nH]cn1]

2. A gadolinium complex represented by the following Formula 2:

[Formula 2]

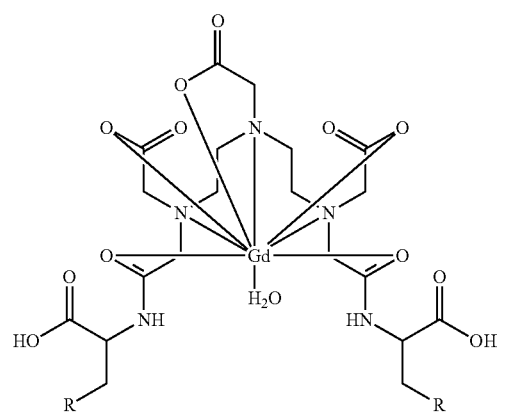

wherein R is

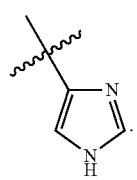

3. A paramagnetic polynuclear metal complex represented by the following Formula 3:

[Formula 3]

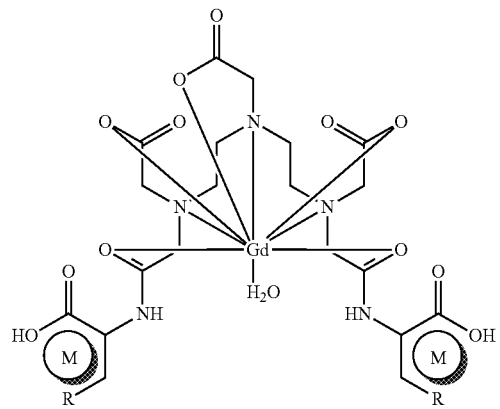

wherein R is

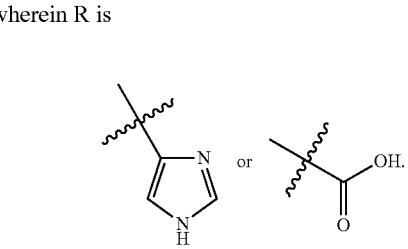

and M is a paramagnetic metal.

4. The paramagnetic polynuclear metal complex according to claim 3, wherein the paramagnetic metal is selected from the group consisting of sodium, potassium, magnesium, calcium, copper, and zinc.

5. A method for preparing the compound represented by Formula 1 of claim 1, comprising the steps of:
 1) adding histidine to DTPA-bis-anhydride, followed by stirring (step 1);
 2) removing a solvent from the mixture prepared in step 1 under low pressure, and then dissolving the resultant in methanol, followed by silica gel chromatography (step 2);
 3) precipitating the resulting compound obtained in step 2 in acetone (step 3); and
 4) drying a substance obtained in step 3 under vacuum to obtain a compound (step 4).

6. A method for preparing a gadolinium complex of the compound represented by the following Formula 2,

[Formula 2]

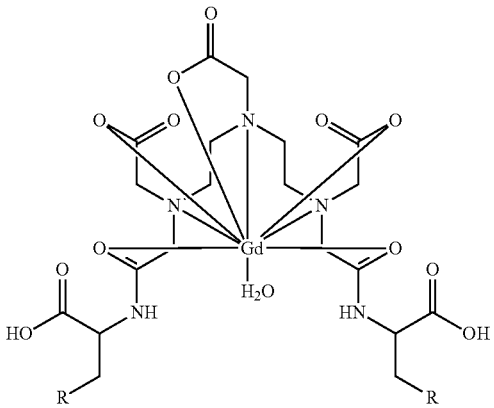

wherein R is

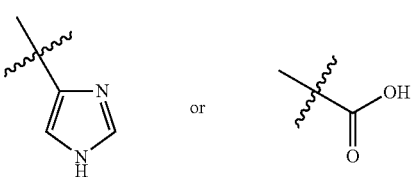

comprising the steps of:
 1) adding the compound represented by the following Formula 1

[Formula 1]

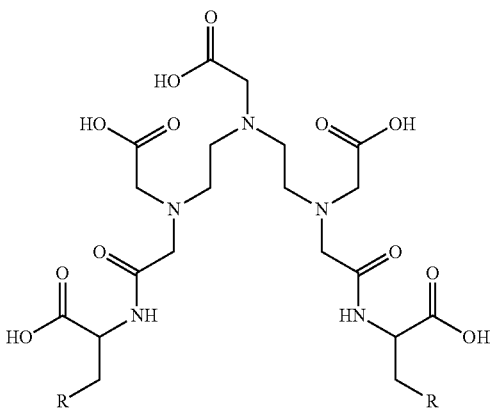

wherein R is

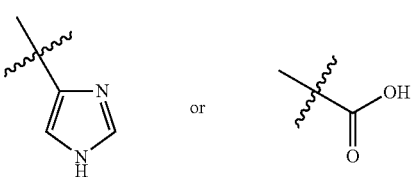

to distilled water, and then adding $Gd_2O_3$ thereto to prepare a solution mixture by stirring (step 1);

2) removing impurities and the solvent from the solution mixture prepared in step 1 (step 2);
3) dissolving the resultant prepared in step 2 in deionized water, and then precipitating it in acetone to obtain a solid.

7. A method for preparing the paramagnetic polynuclear metal complex represented by the following Formula 3,

[Formula 3]

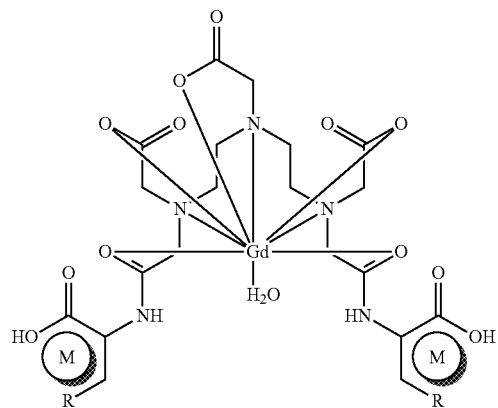

wherein R is

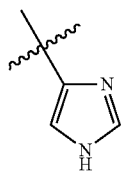 or 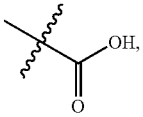

and M is a paramagnetic metal,
comprising the steps of:
1) adding paramagnetic metal ions to the gadolinium complex of the compound represented by the following Formula 2

[Formula 2]

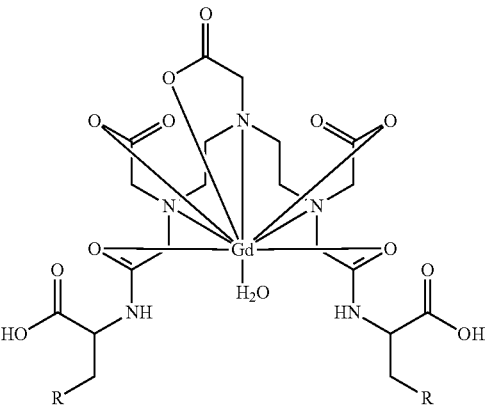

wherein R is

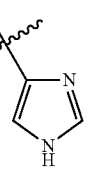 or 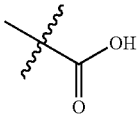

to prepare a solution mixture (step 1); and
2) adding solution mixture prepared in step 1 to acetone for precipitation, and then drying it by filtration to remove the paramagnetic metal ions that are not reacted with the gadolinium complex (step 2).

8. The method according to claim 7, wherein the paramagnetic metal is selected from the group consisting of sodium, potassium, magnesium, calcium, copper, and zinc.

9. A contrast agent comprising the gadolinium complex represented by Formula 2 of claim 2.

10. A contrast agent comprising the paramagnetic polynuclear metal complex represented by Formula 3 of claim 3.

* * * * *